US009060992B2

(12) United States Patent
Sanguinetti et al.

(10) Patent No.: US 9,060,992 B2
(45) Date of Patent: *Jun. 23, 2015

(54) TREATMENT OF SHORT BOWEL SYNDROME PATIENTS WITH COLON-IN-CONTINUITY

(75) Inventors: Elizabeth Lemaire Sanguinetti, Salt Lake City, UT (US); Thomas B. Marriott, Sandy, UT (US); Jennifer Lopansri, Salt Lake City, UT (US); Consuelo Maria Blosch, Mercer Island, WA (US)

(73) Assignee: NPS Pharmaceuticals, Inc., Bedminster, NJ (US)

( * ) Notice: Subject to any disclaimer, the term of this patent is extended or adjusted under 35 U.S.C. 154(b) by 1032 days.

This patent is subject to a terminal disclaimer.

(21) Appl. No.: 12/938,117

(22) Filed: Nov. 2, 2010

(65) Prior Publication Data

US 2011/0172152 A1    Jul. 14, 2011

Related U.S. Application Data

(62) Division of application No. 11/262,980, filed on Nov. 1, 2005, now Pat. No. 7,847,061.

(60) Provisional application No. 60/623,233, filed on Nov. 1, 2004.

(51) Int. Cl.
*A61K 35/38* (2006.01)
*C07K 14/575* (2006.01)
*A61K 38/26* (2006.01)

(52) U.S. Cl.
CPC ..................................... *A61K 38/26* (2013.01)

(58) Field of Classification Search
None
See application file for complete search history.

(56) References Cited

U.S. PATENT DOCUMENTS

| | | | |
|---|---|---|---|
| 5,789,379 A | 8/1998 | Drucker et al. | |
| 6,077,949 A | 6/2000 | Munrose et al. | |
| 6,184,201 B1 * | 2/2001 | Drucker et al. | 514/11.7 |
| 7,411,039 B2 | 8/2008 | Thim et al. | |
| 7,847,061 B2 * | 12/2010 | Sanguinetti et al. | 530/308 |

FOREIGN PATENT DOCUMENTS

| | | |
|---|---|---|
| EP | 1231219 | 8/2002 |
| WO | WO 9639031 | 12/1996 |
| WO | WO 9739091 | 10/1997 |
| WO | WO 9943361 | 9/1999 |
| WO | WO 0149314 | 7/2001 |
| WO | WO 02066511 | 8/2002 |
| WO | WO 2004035624 | 4/2004 |
| WO | WO 2004085471 | 10/2004 |

OTHER PUBLICATIONS

Jeppesen, et al., JPEN, 1999, 23, S101-S105.*
Jeppesen, et al., J. Nutr., 2003, 133, 3721-3724.*
Buchman, 2004, MedGenMed, 6(2), 10 pages.*
Sigalet, 2001, Current Opinion in Investigational Drugs, 2(4), 505-509.*
Burrin, Domestic Animal Endocrinology 24 (2003) 103-122.*
Retrieved from website: 'http://www.yourdictionary.com/negligible' 1 page, retrieved on Jun. 9, 2014.*
Ferrone, et al., "Teduglutide for the treatment of short bowel syndrome", The Annals of Pharmacotherapy, 2006, vol. 40, No. 6, 1105-1109.
International Preliminary Report on Patentability and Written Opinion issued in International Application No. PCT/US2005/039222 dated May 1, 2007.
International Search Report issued in International Application No. PCT/US2005/039222 dated Jul. 17, 2006.
Jeejeebhoy, "Short bowel syndrome: a nutritional and medical approach", CMAJ, 2002, 166(10) 1297-1302.
Jeppesen, et al., "Impaired meal stimulated glucagon-like peptide 2 response in Ileal resected short bowel patients with intestinal failure", Gut, 45:559-563, 1999.
Jeppesen, et al., "Elavated plasma glucagon-like peptide 1 and 2 concentrations in Ileum resected short bowel patients with a preserved colon", Gut, 47:370-376, 2000.
Jeppesen, et al., "Glucagon-like peptide 2 improves nutrient absorption and nutritional status in short bowel-patients with no colon", Gastroenterology, vol. 120, No. 4, 2001, 806-815.
Jeppesen, et al., "ALX-600, a dipeptidyl peptidase-IV resistant glucagon-like peptide-2 (GLP-2) analog, improves intestinal function in short bowel syndrome (SBS) patients with a jejunostomy", Database Biosis (Online) Biosciences Information Service, Philadelphia, PA, Apr. 2002, Database accession No. PREV200200518922.
Jeppesen, et al., "Teduglutide (ALX-0600), a dipeptidyl peptidase IV resistant glucagon-like peptide 2 analogue, improves intestinal function in short bowel syndrome patients", Gut, vol. 54, No. 9, 2005, 1224-1231.
Office Action issued in U.S. Appl. No. 11/262,980 dated Nov. 1, 2006.
Office Action issued in U.S. Appl. No. 11/262,980 dated May 15, 2007.
Office Action (final) issued in U.S. Appl. No. 11/262,980 dated Feb. 4, 2008.
Office Action issued in U.S. Appl. No. 11/262,980 dated Oct. 29, 2008.
Office Action issued in U.S. Appl. No. 11/262,980 dated Aug. 4, 2009.
Request for Continued Examination filed in U.S. Appl. No. 11/262,980 filed Aug. 4, 2008.
Response to Office Action filed in U.S. Appl. No. 11/262,980 filed Mar. 1, 2007.
Response to Office Action filed in U.S. Appl. No. 11/262,980 filed Nov. 15, 2007.
Response to Office Action filed in U.S. Appl. No. 11/262,980 filed Apr. 29, 2009.
Response to Office Action filed in U.S. Appl. No. 11/262,980 filed Jan. 4, 2010.

(Continued)

*Primary Examiner* — Satyanarayana R Gudibande
(74) *Attorney, Agent, or Firm* — Stoel Rives LLP

(57) ABSTRACT

Intestinal absorption is enhanced in short bowel syndrome patients presenting with colon-in-continuity by treatment with a GLP-2 receptor agonist, such as teduglutide.

26 Claims, 2 Drawing Sheets

(56) References Cited

OTHER PUBLICATIONS

Response to Restriction Requirement filed in U.S. Appl. No. 11/262,980 filed Oct. 11, 2006.
Restriction Requirement issued in U.S. Appl. No. 11/262,980 issued Sep. 11, 2006.
Scott, et al., "GLP-2 Augments the adaptive response to massive intestinal resection in rat", Am. J. Physiol. (Gastrointestinal Liver Physiology 38): G911-G921, 1988.
Yang, et al., "Novel Agents in the treatment of intestinal failure: humoral factors", Gastroenterology, vol. 130, No. 2, 2006, S117-S121.
Teduglutide, (online), NPS Pharmaceuticals, Oct. 3, 2003, accessed May 16, 2011, http://replay.web.archive.org/20031003111216/http://www.npsp.com/drug_development/dd_alx0600.php.

* cited by examiner

TREATMENT OF SHORT BOWEL SYNDROME PATIENTS WITH COLON-IN-CONTINUITY

FIELD OF THE INVENTION

This invention relates to products and methods useful medically to treat patients presenting with short bowel syndrome. More particularly, the invention relates to glucagon-like peptide 2 (GLP-2) and other GLP-2 receptor agonists effective to improve intestinal function particularly in patients presenting with short bowel syndrome with colon-in-continuity.

BACKGROUND TO THE INVENTION

The estimated prevalence of short bowel syndrome (SBS) patients with non-malignant disease requiring home parenteral nutrition (HPN) is at least 40 per million of the U.S. population. SBS usually results from surgical resection of some or most of the small intestine for conditions such as Crohn's disease, mesenteric infarction, volvulus, trauma, congenital anomalies, and multiple strictures due to adhesions or radiation. Surgical resection may also include resection of all or part of the colon. SBS patients suffer from malabsorption that may lead to malnutrition, dehydration and weight loss. Some patients can maintain their protein and energy balance through hyperphagia; more rarely they can sustain fluid and electrolyte requirements to become independent from parenteral fluid.

Although long-term parenteral nutrition (PN) is life saving in patients with intestinal failure, it is expensive, impairs quality of life and is associated with serious complications such as catheter sepsis, venous occlusions and liver failure. Treatments that amplify absolute intestinal absorption, and eliminate or minimize the need for PN have great potential significance to SBS patients.

The endogenous meal-stimulated hormone, glucagon-like peptide-2 (GLP-2), raises considerable interest for SBS patients. GLP-2 functions to slow gastric emptying, reduce gastric secretions, increase intestinal blood-flow and stimulate growth of the small and large intestine. In animal studies, GLP-2 administration induces mucosal epithelial proliferation in the stomach and small and large intestine by stimulation of crypt cell proliferation and inhibition of enterocyte apoptosis.

SBS patients with end-jejunostomy and no colon have low basal GLP-2 levels and limited meal-stimulated GLP-2 secretion due to removal of GLP-2 secreting L-cells, which are located primarily in the terminal ileum and colon. This GLP-2 deficiency results in a minimal adaptive response following resection and could explain the gastric hypersecretion, rapid intestinal transit and lack of intestinal adaptation observed in these SBS patients.

Jeppesen et al. (Gastroenterology 2001; 120:806-815) have described positive benefit in an open-label study using pharmacologic doses of native GLP-2 in SBS jejunostomy patients. There was significant improvement in intestinal wet weight absorption and a more modest improvement in energy absorption that led to an increase in body weight, lean body mass and a rise in urinary creatinine excretion.

In contrast, SBS patients with colon-in-continuity have elevated basal endogenous GLP-2 levels resulting in an adaptive response to resection characterized by improved wet weight gain and energy absorption. The potential for added benefit of pharmacologic doses of GLP-2 receptor agonists in these patients is not obvious and has not been studied.

SUMMARY OF THE INVENTION

It has now been determined that intestinal absorption is enhanced in SBS patients presenting with colon-in-continuity when those patients are treated with a GLP-2 receptor agonist.

Thus, in one aspect, the present invention provides a method for enhancing intestinal absorption in a patient with short bowel syndrome, comprising the steps of selecting for
treatment a short, bowel syndrome patient presenting with at least about 25% colon in continuity with remnant small intestine, and treating said patient with a GLP-2
receptor
agonist to enhance intestinal absorption by said patient.

In a related aspect, the present invention provides for the use of a GLP-2 receptor agonist in the preparation of a medicament for enhancing intestinal absorption in short bowel syndrome patients presenting with at least about 25% colon in continuity with remnant small intestine.

In a preferred embodiment, the GLP-2 receptor agonist is [Gly2]hGLP-2, known as teduglutide.

BRIEF REFERENCE TO THE DRAWINGS

Embodiments of the invention are now described with reference to the accompanying drawings in which.

DETAILED DESCRIPTION

Figure 1:
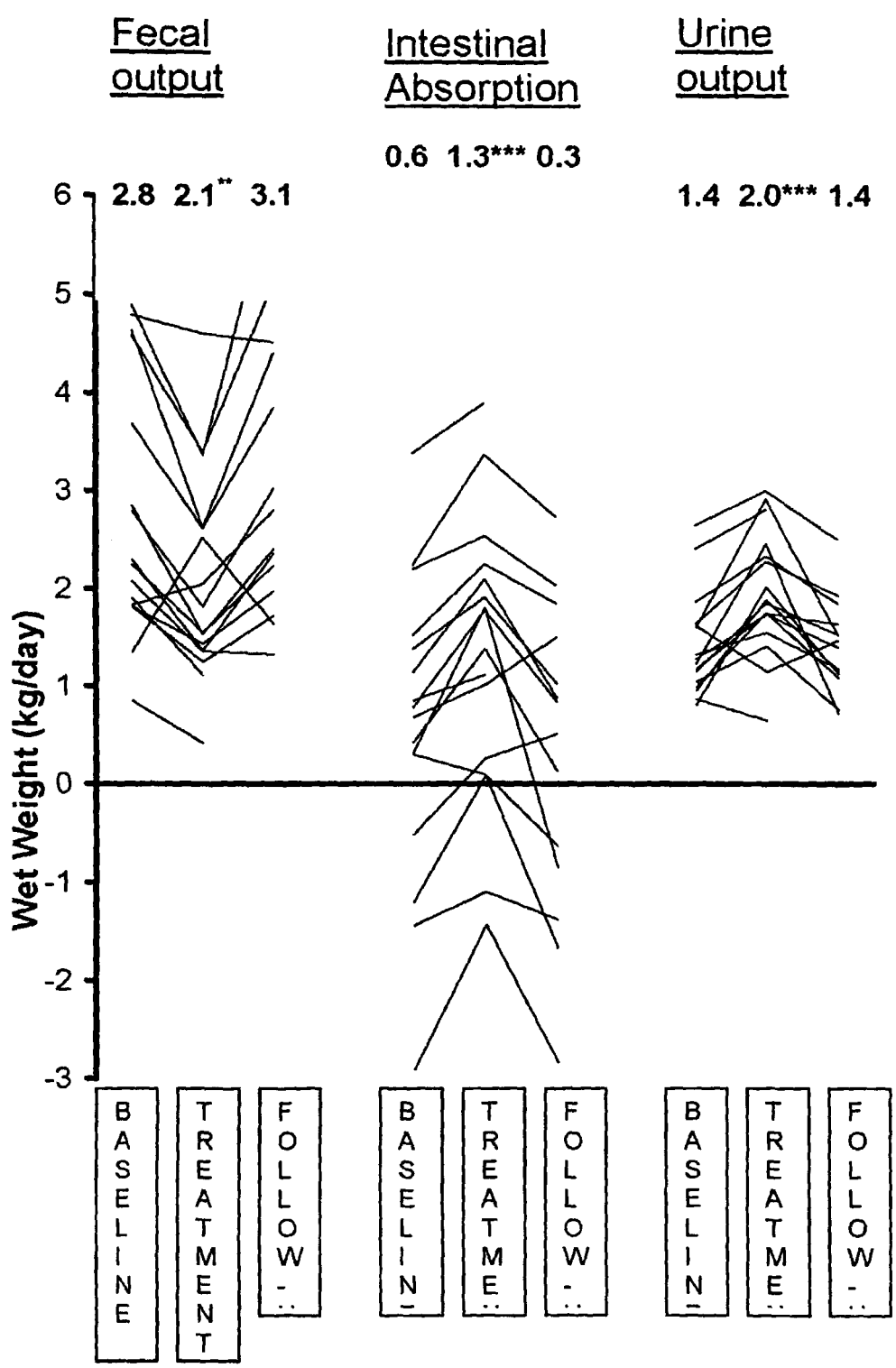
FIG. 1 illustrates results measured in terms of fecal wet weight, intestinal wet weight absorption and urine weight in the individual patients at Baseline (Days—3 to 0), during treatment (Days 18 to 21), and at follow-up (Days 39 to 42).

The positive effect of GLP-2 receptor agonists on intestinal absorption in SBS patients that retain at least some, e.g., >25%, of their colon is particularly surprising. These patients have essentially retained GLP-2 producing tissue and, indeed, show elevated basal levels of the endogenous GLP-2 that can be as high as meal stimulated levels in normal, healthy individuals and that, in normal individual, is responsible for maintenance of the intestinal lining required for intestinal absorption. There is nevertheless significant clinical benefit for these patients, manifest principally as enhanced intestinal absorption as indicated by increased absolute wet weight absorption, when they are treated in accordance with the present method.

More particularly, patient candidates for the present treatment are those presenting with SBS resulting from small intestine resection which may be secondary to Crohn's disease, vascular ischemic disease, malrotation or volvulus, trauma, congenital anomalies, or multiple strictures due to adhesions or radiation and who require parenteral nutrition to meet their needs. As patients presenting with short bowel syndrome, such patients typically retain, following resection, a length of small intestine that is within the range from at least about 25 cm and at most about 200 cm., e.g., from about 50-150 cm. Such SBS patients include those patients presenting with jejunostomy, in which part of the jejunum is resected and generally all of the ileum, and/or ileostomy in which part of the ileum is resected and the jejunum may or may not be present. SBS patients with jejunostomy or ileostomy generally do not have any remaining colon, but if they do, it is not in continuity with the remnant small intestine.

SBS patients selected for treatment by the present method are those who retain, in continuity with remnant small intestine, at least some length of their colon, such as at least about 25%, and desirably 30%, 35%, 40%, 45% and preferably at least 50%, 60%, 70%, 80%, 90% or more. The remaining length of colon typically will be determined from the surgical records of a patient candidate. Expressed in other terms, preferred candidates for the present treatment are short bowel syndrome patients who retain colon sufficient to produce endogenous GLP-2 at levels that are at least greater than the negligible levels produced by patients with no colon, and ideally are similar to those GLP-2 levels produced by healthy volunteers. Endogenous GLP-2 levels for normal, healthy individuals are 15±2 pmol/L fasted, and 61±19 pmol/L fed. Candidates for the present treatment thus are SBS patients that retain sufficient functional colon to produce at least about 10%, 20%, 30%, 40%, 50% or more of such levels in the fed state, e.g., at least about 5 pmol/L fed, and desirably 10, 15, 20, 25, 30, 35, 40, 45, 50, 55, 60, 65 and 70 pmol/L endogenous GLP-2 in the fed state.

In a preferred embodiment, treatment candidates are those short bowel syndrome patients who retain at least 50% or more of colon length in continuity with remnant small intestine. Such a treatment candidate is identified herein as a patient with ≥50% colon-in-continuity. In other preferred embodiments, the SBS patient with colon in continuity has a remnant small intestine at least about 50 cm in length which, desirably but not essentially, incorporates at least a portion of the ileum.

The patients can be selected for treatment by the present method at any time following the surgical resection. That is, patients that are undergoing adaptation, as well as those who have had sufficient time to adapt following the surgery, are acceptable treatment candidates.

Treatment of short bowel syndrome patients presenting with colon-in-continuity, in accordance with the present method, is effective to enhance intestinal absorption, particularly of fluid including water and salts, but including nutrients as well. This effect is revealed particularly as a treatment-mediated, statistically significant increase in absolute wet weight absorption, which is determined by subtracting fecal wet weight from diet wet weight using a vigorous nutrient absorption test. The effect of treatment is also generally seen as a reduction in fecal wet weight, an increase in urine wet weight, a reduction in energy excretion (measured as herein described), and in other respects noted in the examples herein.

The present treatment method entails dosing the selected patient with a GLP-2 receptor agonist using a treatment regimen effective to enhance intestinal absorption. Such GLP-2 receptor agonists are characterized as molecules that bind with, preferably selectively, and stimulate the human GLP-2 receptor, as reported by Monroe et al. in U.S. Pat. No. 6,077, 949 issued Jun. 20, 2000, incorporated herein by reference. Briefly, GLP-2 receptor agonists are revealed as agents that trigger production of, or trigger an elevation in the level of, a second messenger coupled to the human GLP-2 receptor, when exposed to a host cell that produces that receptor naturally or is transfected with DNA encoding that receptor.

In one embodiment of the invention, the GLP-2 receptor agonist is human GLP-2. In other embodiments, the GLP-2 receptor agonist is a vertebrate, e.g., mammalian, homolog of human GLP-2. Thus, GLP-2 receptor agonists useful in embodiments of the present invention include GLP-2 having the sequence found in GLP-2 endogenous to human, cow, pig, primate, sheep, rodents including mouse, rat, degu and the like, and other vertebrate species.

In other embodiments, the GLP-2 receptor agonist is an analog of human GLP-2, which incorporates at least one, and usually not more than 5, e.g., 1, 2 or 3, amino acid substitutions or additions, and may also have a C-terminal truncation of from 1 to 5 or more amino acids.

In a preferred embodiment, the GLP-2 receptor agonist is a GLP-2 peptide analog that is altered to prolong serum half-life. In a particularly preferred embodiment, the GLP-2 peptide incorporates an amino acid substitution that renders the peptide resistant to the endogenous enzyme dipeptidyl peptidase IV (DPP-IV). Such analogs incorporate an appropriate substitution of the Ala2 residue desirably, but not essentially, by a genetically encoded amino acid, to permit recombinant production of the desired protein. Amino acids that can usefully substitute at Ala2 to provide GLP-2 analogs that retain GLP-2 receptor agonist activity and are less susceptible to DPP-IV include GLy, D-Ala, Val, Glu, Lys, Arg, Leu and Ile. Still other GLP-2 analogs include those substituted at Met10 by an amino acid that is less sensitive to oxidation.

In alternative embodiments, the GLP-2 peptide, or GLP-2 peptide analog is derivatized, for instance at an internal or substituted lysine, to prolong serum half-life by conjugation with lipophilic groups, with polyethylene glycol groups, with albumin or with any other functional group having the desired effect of reducing the rate at which the peptide is degraded endogenously following its administration. Such derivatized forms may be derivatized analogs of GLP-2, which carry substitutions, such as conserved or non-conserved lysine substitutions, having no appreciable negative effect on GLP-2 receptor activation but allowing for conjugation of the desired functional group. It will be appreciated that these derivatized forms of GLP-2 or of GLP-2 analogs are considered to be GLP-2 receptor agonists if they exert their endogenous effect through the GLP-2 receptor after administration, even if this GLP-2 receptor agonist property is not displayed while in the pro-drug, pre-administration form.

A wide variety of useful active GLP-2 analogs and derivatives have been described in the literature, as revealed in U.S. Pat. No. 5,789,379 issued Jun. 20, 2000 and related WO97/39031 published Oct. 23, 1997 which teach site-specific GLP-2 analogs; in WO02/066511 published Aug. 27, 2003 which teaches albumin-derivatized forms of GLP-2 and analogs, and in WO99/43361 published Oct. 14, 1999, WO04/035624 published Apr. 29, 2004 and WO04/085471 published Oct. 7, 2004 which describe lipophilic-derivatized forms of GLP-2 and analogs.

In a particularly preferred embodiment of the present invention, the GLP-2 receptor agonist is [Gly2]hGLP-2, known as teduglutide.

The dosing regimen effective to treat the SBS patients with colon-in-continuity entails delivering the selected GLP-2 receptor agonist to the patient for a time and at a dose sufficient to enhance intestinal absorption. As noted in the examples herein, and according to a preferred embodiment of the present invention, one suitable treatment regimen entails once daily administration of teduglutide, by subcutaneous injection in the abdomen, thigh or arm, at a dose in the range from 30 to 150 ug/kg/day for a period of about 21 days. It is anticipated that effective daily doses of teduglutide, as well as human GLP-2 per se and other GLP-2 receptor agonist with comparable properties, will lie generally in the broader range from about 5 to 500 ug/kg/day e.g., from 10 to 400 ug/kg/day, such as 20 to 300 ug/kg/day.

It will be appreciated from these results that a similarly beneficial effect can be expected when using either teduglutide, or when using a related GLP-2 receptor agonist, in an alternative dosing schedule. With respect to teduglutide per se, administration twice daily or still more frequently can be beneficial. Twice daily (every 12 hours) dosing usefully delivers about 5 to 250 ug/kg/dose. Benefits can also accrue to schedules that entail shorter or, more desirably, longer term dosing, such as from about 14 days to many months or even years. Maintenance dosing also is desirable, in which patients receive either continued or follow up dosing. Follow-up dosing usefully occurs at regular frequencies such as weekly, biweekly, every month, every three months, etc. Continued dosing usefully provides to the patient a dose efficient to maintain the benefits of increased absorptive surface area with increased intestinal absorption that arise from initial treatment, and can be effected by dosing the patient at least once within every 1-28 days, e.g., every other day, 2-3 times per week, once per week, etc. Continued or follow-up dosing can be important to preserve the medical benefits mediated by the GLP-2 receptor agonist; as noted in the examples, improvements in intestinal absorption following treatment with teduglutide for instance, can be lost rapidly, for example within four weeks following cessation of dosing.

The teduglutide dosing regimen herein described is useful to determine effective dosing schedules for other GLP-2 receptor agonists for which pharmacokinetics properties are either already known or can be determined, by relating pharmacologic, pharmacokinetic and pharmacodynamic properties, in accordance with standard practise in drug development.

It will be appreciated that the route of administration, and the particular dosage form of the GLP-2 receptor agonist, will be chosen to preserve and desirably optimize the effect of the drug. Administration by injection, such as subcutaneous, intramuscular, intravenous, etc., is suitable. Alternatively, the drug may be administered by infusion or by any other route that delivers the drug to the target site on the serosal side of the intestinal tissue, such as by depot injection. If delivered by injection, the drug can be formulated as a lyophilized powder for reconstitution by the user, and as either unit or multiple doses. One formulation of teduglutide, for instance, is described in WO01/49314 published Jul. 12, 2001, and provides a powder for reconstitution in which teduglutide is present with L-histidine, mannitol and sodium phosphate. This is usefully provided as a 3 mL glass vial containing 10 mg teduglutide, for reconstitution with 1 mL water for injection and self-administration. An alternative formulation provides 10 mg of teduglutide in a smaller volume of aqueous vehicle, such as 0.5 mL water for injection.

Most suitably, the chosen treatment parameters, including choice of GLP-2 receptor agonist, and dosing schedule, are selected to provide optimal enhancement of intestinal absorption, e.g. to provide for an increase in the volume of fluid and the nutrients absorbed by the patient, which is revealed for instance as a decrease of at least about 5%, 10%, 15%, 20% or more in fecal wet weight, and/or an increase of at least about 5%, 10% or more in urine weight.

Embodiments of the invention are exemplified below:

Patients

Study subjects were recruited from centers in the U.S. and Denmark that care for patients receiving PN. All patients had undergone extensive resection of the small intestine without any surgical resection of the stomach, duodenum or pancreas.

Study inclusion criteria were: Over 18 years of age; diagnosis of SBS that could be secondary to Crohn's disease, volvulus, injury or vascular ischemia, remnant small intestine of 150 cm or less; no clinical evidence of active inflammatory bowel disease (IBD) or fistulas; no history of radiation enteritis, or sprue; no alcohol or drug abuse; no significant renal, hepatic or cardiac diseases; no glutamine for at least four weeks prior to screening; no growth factors or participation in any clinical trial within three months of screening (except use of teduglutide in patients in the rechallenge group). SBS patients with ≥50% colon-in-continuity had a demonstrated fecal weight exceeding 1 kg/day and fecal energy loss exceeding 2 MJ/day [478 Kcal/day].

Women of childbearing age had to have a negative blood β-human chorionic gonadotropin test before inclusion in the study and used effective contraceptives during the study. Usual medications such as proton pump inhibitors, codeine, loperamide, and oral and parenteral supplements were kept constant. Local Ethics Committees or Institutional Review Boards approved the protocol. Procedures were in accordance with ethical standards of the Helsinki Declaration of 1964 as modified by the 48$^{th}$ World Medical Association in 1996. Each eligible patient signed an informed consent form prior to study.

Study Protocol

This was an open-label, pilot study to determine the safety and effect of teduglutide in patients with short bowel syndrome (SBS). The patient's history was reviewed and a physical examination performed to determine eligibility before inclusion in the study. Estimated residual small intestine and colon lengths were determined by reviewing operative reports and available radiographic studies. Eligible patients were admitted as inpatients to hospital wards or General Clinic Research Centers (GCRC) on three separate occasions, 18 days apart, for the last four days and three nights of the baseline period and at the end of the treatment and follow-up periods. Treatment consisted of recombinant teduglutide (supplied by NPS Allelix, Mississauga, ON, Canada) formulated as a lyophilized powder with L-histidine, mannitol, and monobasic and dibasic sodium phosphate (Lot 8502901). Water was added to reconstitute the drug for administration by subcutaneous (s.c.) injections in the abdomen or thigh. Ten SBS patients with jejunostomy received 0.03 mg/kg/d, 0.10 mg/kg/d or 0.15 mg/kg/d once daily for 21 days. Five SBS patients with ≥50% colon-in-continuity received teduglutide 0.10 mg/kg/d once daily for 21 days. During each inpatient period, patients underwent 72-hour nutrient balance and D-Xylose absorption studies, and a proximal or distal endoscopy to ascertain the condition of the intestinal mucosa and obtain biopsy samples. In jejunostomy patients, biopsies were obtained through the jejunostomy stoma or by upper gastrointestinal endoscopy. In patients with colon-in-continuity, colo-rectal biopsies were obtained. Teduglutide treatment began on Day 1 (immediately after the baseline period) and continued once-daily for 21 days. On the first and last day of dosing, all patients had blood collections for plasma levels and pharmacokinetic parameters and to test for any antibodies to teduglutide or E. coli protein. Patients were monitored for safety (adverse events, physical exams, vital signs, ECGs, laboratory results, and injection site examinations) during the inpatient periods and during outpatient visits on days 7 and 14.

The 72-hour nutrient balance studies were completed with each patient eating their usual diet, calculated from a seven-day food diary completed by the patient during the screening period. It was intended that patients eat the same quantity and quality of food and beverages during each admission. During the 72-hour balance periods, all oral intake (duplicate meals and beverages and declined food), fecal/stomal output, and urine were collected and weighed. All stool samples were refrigerated during the collection period. Stools and diets were separately homogenized and analyzed for energy content (by bomb calorimetry), nitrogen (by the macro-Kjeldahl's method), fat (by the gravimetric technique), and sodium and potassium (by atomic absorption).

D-Xylose was used to test intestinal carbohydrate absorption. After an overnight fast, patients drank a test solution of 25 g D-Xylose in 200-mL distilled water over a 2-3 minute period. A blood sample was taken at two hours and urine collected for 5-hours following ingestion.

Morphological Analysis

Endoscopic examinations were performed in each subject at the completion of baseline, treatment and follow-up phases. All tissue samples for measurement of villus height and crypt depth were prepared and analyzed in a blinded fashion by the same pathologist. Villus height and crypt depth were measured using light microscopy (eyepiece micrometer) as the mean of ten well-oriented villi and crypts. The number of mitotic figures per 100 crypt epithelial cells was calculated.

Statistics

Using the SAS (Version 8.2; SAS Institute, Cary, N.C.) statistical program, a Student's paired t test was employed that compared treatment to baseline values, and follow-up to baseline values. No comparisons were made between patients on different doses or with different anatomy due to the limited number of patients in the study. Data are expressed as mean±SD. A value of $p<0.05$ was considered significant.

Results

Patients

Sixteen SBS patients (nine females, seven males) enrolled in this open-label, multicenter, dose-ranging pilot study and received teduglutide. Four U.S. sites recruited 6 patients and one Danish site recruited 10 patients. The baseline characteristics of these 16 patients treated are given in Table 1. These patients were subdivided into an end-jejunostomy group of 10 (Group 2) and ≥50% colon-in-continuity group of 5 (Group 3). There were originally 11 jejunostomy patients, but patient 03 was found on biopsy to have a remnant segment of colon, later estimated to be 30%. This individual was not included in any subgroup analysis. As judged from analysis of duplicate meals adjusted for declined food, some patients had better dietary consistency than others. Patients who had an oral food intake where the dietary wet weight and energy content at treatment did not differ more than 10% from baseline values were termed "high dietary compliance". Ten patients had a high dietary compliance (<10% variability from baseline value), 5 with end jejunostomy and 5 with ≥50% colon-in-continuity (Group 4).

The demographics of the two groups of SBS patients, those with end jejunostomy and those with colon-in-continuity, were similar with ages ranging from 27-74 years, weights ranging from 38.9-79.2 kg, heights ranging from 158-180 cm, BMI ranging from 15.0-26.9 kg/m$^2$, years since last intestinal resection ranging from 2.4-20 years (except one patient 0.9 years post-resection, whose results were similar to others who received 0.15 mg/kg/day), and remnant jejunum lengths ranging from 25-150 cm. The causes for intestinal resection were Crohn's disease (11), mesenteric infarction (2), volvulus (1), stricture (1), and trauma (1). Twelve of the 16 SBS patients used anti-diarrheal medications, and 14 patients used anti-secretory medications, including one that took octreotide. Of the 15 patients who had evaluable data, 3 patients with colon-in-continuity did not require either PN or fluids, 2 end jejunostomy patients required fluids only, and 10 patients required both PN and fluids (Table 1).

Compliance

Jejunostomy patient 03, who was found to have a segment of colon-in-continuity, and patient 20, known to have colon-in-continuity, did not complete the follow-up period. Drug compliance (counting the number of returned vials) was complete in all patients participating during the nutrient balance periods. During the 21 day treatment period, drug compliance was complete, except in one patient with colon-in-continuity, who administered the full dose for 15 days, half-doses for two days, and no dose for four days.

Safety Results

All patients were monitored for safety. There were no deaths and no withdrawals due to adverse events (AEs). Two patients with evaluable data reported a serious AE of catheter-related infection or catheter-related complication following dosing. None of these were judged to be related to teduglutide. The incidence of AEs was similar between groups. The most common AEs were edema of the lower limbs, and localized swelling of the jejunostomy nipple. Other AEs included headache and abdominal pain. Three patients had minor injection site reactions (single events of bruising, induration, rash; four events of erythema). No clinically significant abnormal laboratory values were identified in relation to teduglutide treatment. No safety concerns were raised from vital signs or ECGs. No antibodies to teduglutide were detected. One patient had a relative *E. coli* protein antibody titer of 1:1624, and six patients had relative titers between 1:107 and 1:228, after treatment.

Endogenous GLP-2 Levels

For patients with ≥50% colon-in-continuity, fasting concentrations of endogenous GLP-2 were measured prior to administration of teduglutide. For four of the five subjects, their concentrations were between the mean levels for fasted and fed healthy volunteers (fasted (15±2 pmol/L) and fed (61±9 pmol/L)), measured as described by Hartmann et al. (Peptides 21 2000; 73-80, incorporated herein by reference). The levels for the five subjects were 16, 27, 37, 41, and 73 pmol/L.

Effects of Teduglutide

Wet Weight

FIG. 1 illustrates fecal wet weight, intestinal wet weight absorption and urine weight in the individual patients in Groups 2 and 3 at baseline, during treatment and at follow-up. A 21-day treatment with teduglutide significantly decreased fecal wet weight, compared to baseline, in each subgroup (Groups 2 and 3; Table 2). The decrease was similar in those with end jejunostomy (Group 2, 682±911 g/d, p=0.040) and those with colon-in-continuity (Group 3, 822±341 g/d, P=0.006). Absolute wet weight absorption was obtained by subtracting fecal wet weight from diet wet weight. Teduglutide increased absolute wet weight absorption in all 15 SBS patients compared to baseline. These increases were significant for all groups and closely reflected the decreases in fecal output. The absolute wet weight absorption increased as a percent of intake in 13 of 15 SBS patients. The increase in the relative absorption was similar for SBS patients with end jejunostomy (Group 2, 20±18%, p=0.007) and those with ≥50% colon-in-continuity (Group 3, 26±16%, p=0.023). As expected from increases in intestinal wet weight absorption, teduglutide increased urine weight in 13 of 15 SBS patients. Similar increases were seen in those patients with end-jejunostomy (Group 2, 680±535 g/d, p=0.003) and those with ≥50% colon-in-continuity (Group 3, 461±200 g/d, p=0.007).

Energy

Figure 2:
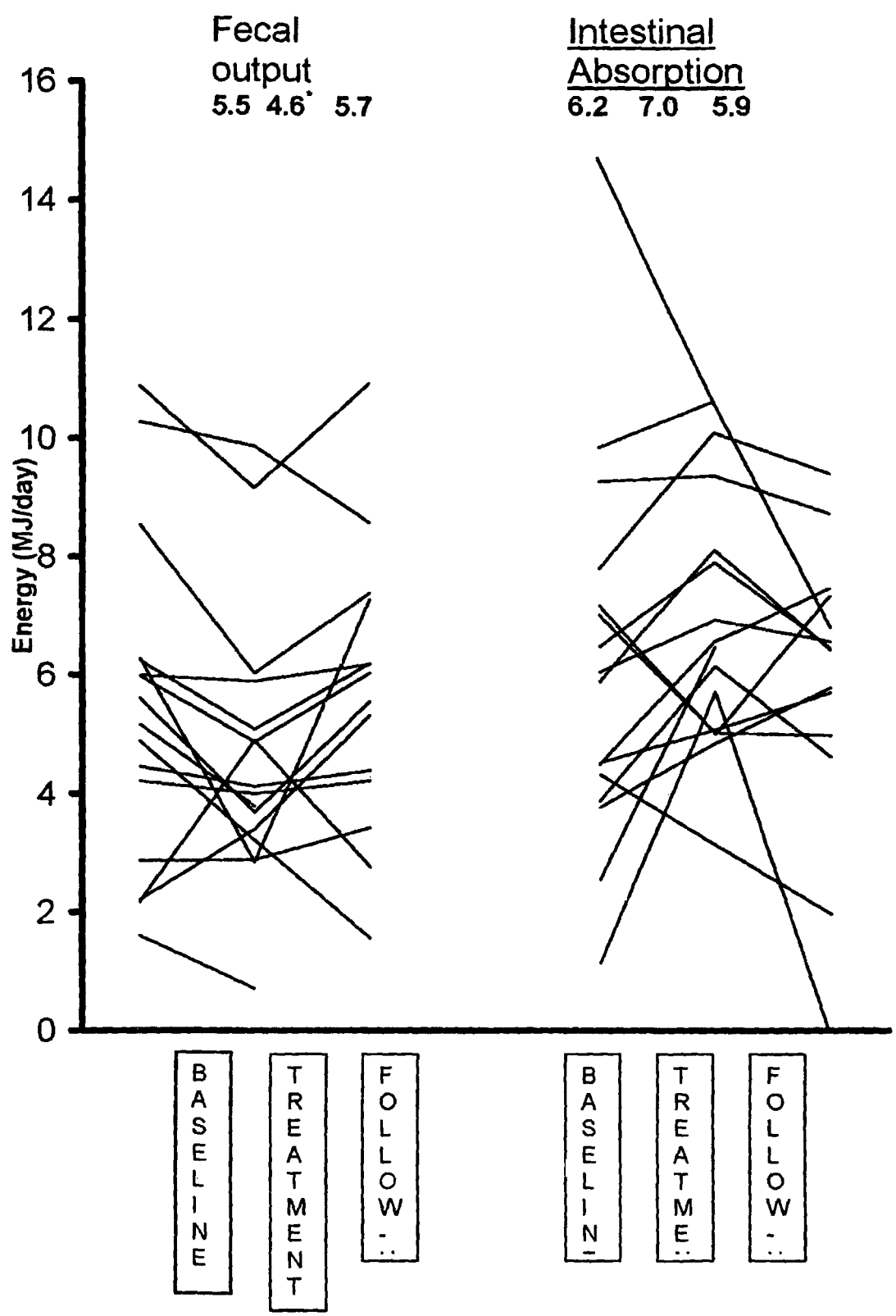
FIG. 2 illustrates results measured in terms of fecal energy excretion and intestinal absorption in the individual patients at Baseline (Days—3 to 0), during treatment (Days 18 to 21), and at follow-up (Days 39 to 42).

FIG. 2 illustrates fecal energy excretion and intestinal energy absorption in the individual patients at baseline, during treatment and at follow-up. Compared to baseline, the 12 of 15 SBS patients had significant decreases in energy excretion on teduglutide. This reduction was more pronounced in those with colon-in-continuity (Group 3, 1343±916 kJ/d, p=0.031) and those with high dietary compliance (Group 4, 1060±1083 kJ/d, p=0.013) than those with end jejunostomy (Group 2, 532±1703 kJ/d, p>0.05). Significant effects were also seen with improved energy absorption (Group 3, 1027±798 kJ/d, p=0.045; Group 4, 963±1290 kJ/d, p=0.043) and relative energy absorption (Group 3, 10±7%, p=0.030; Group 4, 8±11%, p=0.040).

Biopsies

Significant histological changes in relation to teduglutide treatment were seen in the jejunum in 7 of the 8 Group 2 patients who were biopsied. There was an increase in villus height (38±45%, p=0.030), crypt depth (22±18%, p=0.010), and mitotic index (115±108%, p=0.010). These results indicate structural changes corresponded with observed improved absorption. Small intestine biopsies were not obtained from patients with colon-in-continuity (Group 3), however colonic biopsies for measurements of colonic crypt depth were obtained from these patients. Crypt depth increased in four of five sets of colonic biopsies following teduglutide treatment, but the mean increase of 13±22% did not reach statistical significance (p=0.330) and the increase in mitotic index was not significant (76±112%, p=0.170). Most changes in intestinal absorption and histology related to teduglutide treatment had reversed at follow-up.

Discussion

The main findings in this study were the considerable effects of the GLP-2 receptor agonist, teduglutide ([Gly2] hGLP-2), on reducing intestinal wet weight excretion and improving wet weight absorption in SBS patients. These effects were even seen with the SBS patients with colon-in-continuity, most of whom had increased endogenous GLP-2 concentrations. The 10 end jejunostomy SBS patients had significantly increased absolute (788±551 g/day, p<0.01) and relative (20±18%, p<0.01) wet weight absorption, increased urine production of 680±535 g/day (p<0.01) and decreased fecal wet weight excretion of 682±911 g/day (p<0.05). Effects of equal magnitude were seen in SBS patients with ≥50% colon-in-continuity: significantly increased absolute (751±328 g/day, p<0.001) and relative (26±16%, p<0.05) wet weight absorption, increased urine production of 461±200 g/day (p<0.01) and decreased fecal wet weight excretion of 822±341 g/day (p<0.01). These remarkable effects were seen in steady-state SBS patients, who were optimally treated with conventional antisecretory and anti-diarrheal medication.

The effects of teduglutide on wet weight absorption were almost two-fold those observed in the pilot study of another GLP-2 receptor agonist, native GLP-2, for 35 days (420±480 g/day, p=0.040), conducted in patients with similar baseline wet weight absorption. This greater effect could be related to differences in dose and half-life of GLP-2 and teduglutide, respectively. In the pilot study with native GLP-2, 400 µg was given twice daily (corresponding to 0.013±0.002 mg/kg/day, a range of 0.011-0.017 mg/kg/day). The teduglutide doses in the current study were 3-10 times higher, ranging from 0.03 to 0.15 mg/kg/day. Replacement of alanine by glycine in position 2 of GLP-2 blocks degradation by DPP-IV, extending the half-life from approximately seven minutes (GLP-2) to approximately 0.9 to 2.3 hours (teduglutide). If area under the curve (AUC) is critical for the wet weight absorption effect, the AUC during teduglutide treatment may well be 200 times greater than the AUC when using native GLP-2. In this study, effects of teduglutide on energy and macronutrient absorption were minor compared to effects on wet weight absorption. Although decreases in the fecal energy excretion of 532±1703 kJ/d, (p>0.05) and 1343±916 (p<0.05) were demonstrated in SBS patients with end jejunostomy and colon-in-continuity, respectively, this did not translate into significant increases in absolute or relative energy absorption. Nonetheless, the effect of teduglutide on absolute energy absorption is 1.5 to 4-fold higher than with native GLP-2 (441±634 kJ/day ([105±151 kcal/day] p=0.09) at the given doses and treatment periods. Thus, in contrast to $H_2$-receptor antagonists, proton-pump inhibitors and octreotide that only affect wet weight absorption, native GLP-2 and teduglutide seem to affect both intestinal wet weight and energy absorption, with an additional positive effect on wet weight absorption in patients already treated with these non-GLP-2 agonists.

Several physiological mechanisms may account for the positive effects seen on intestinal absorption with teduglutide treatment. SBS patients with end-jejunostomy, who have limited or no endogenous meal-stimulated GLP-2 secretion, often suffer from gastric hypersecretion and rapid gastric emptying, at least initially after enterectomy. GLP-2 has been shown to diminish gastric acid secretion in sham-fed healthy humans and prolong gastric emptying in SBS patients. Therefore, it is likely that a pharmacological replacement may restore the physiological feedback, previously described as the ileal break mechanism. This is the first human study demonstrating the intestinotrophic properties of a GLP-2 analog. No other pharmacological agents have been able to promote a significant adaptation of this magnitude, possibly as a result of increasing the absorptive surface area of the intestine. In the SBS patients with end-jejunostomy, teduglutide significantly increased small intestine villus heights (38±45%, p=0.030), crypt depth (22±18%, p=0.010), and mitotic index (115±108, p=0.010).

The mechanisms regarding the effect of teduglutide in SBS patients with colon-in-continuity are more speculative. These patients have continuously high endogenous GLP-2 secretion, with normal gastric secretion and emptying. However, the supraphysiological doses of teduglutide may produce local high concentrations that suppress gastric secretion and induce small intestine growth. Small intestine biopsies were not obtained in these patients. In SBS patients with and without colon-in-continuity, an up-regulation of transport proteins is possible as described in animal studies.

Regardless of the exact physiological mechanism, increases in intestinal absorption in relation to treatments that improve intestinal adaptation would preferably be converted into positive effects regarding body weight or composition, hydration, physical activity, and ultimately, quality of life. The latter two points were not examined in either study quoted here. Body weight did not significantly increase following teduglutide treatment (0.9±2.1 kg, p=0.120).

The type and severity of adverse events will be an important issue when considering long-term treatment in SBS patients. In this population, the serious AEs were related to the underlying condition and the AEs were mainly related to the pharmacodynamic effects of teduglutide. The increase in intestinal wet weight absorption may contribute to peripheral edema, which can be treated by reducing parenteral volume.

The pharmacodynamics of teduglutide appear to be intestine-specific and the AEs are limited, therefore teduglutide may have a role in the long-term treatment of SBS patients. The 0.75 L of improved wet weight absorption has significant clinical implications for this SBS patient population (e.g., less PN or fewer days/weeks). Spending less time on parenteral infusions may be valuable for the quality of life in these patients. The non-PN dependent SBS patients may also be candidates for this treatment. Many of these patients suffer from repeated episodes of dehydration, renal insufficiency and kidney stones. Increasing the wet weight absorption in these patients may diminish well-known complications of SBS.

TABLE 1

Patient Characteristics

| Patient ID | Dose mg/kg/day | Gender/Age (years) | Diagnosis | Remnant small intestine (cm) and colon (%) (cm/%) | Baseline Fecal Weight (kg/d) | Baseline Fecal Energy (kJ/d) | Parenteral Fluid (g/day) | Parenteral Energy (kJ/day) | Dietary Compliance, Wet weight (%) | Dietary Compliance, Energy (%) | Group of Patients |
|---|---|---|---|---|---|---|---|---|---|---|---|
| 01 | 0.03 | F/56 | CD | 130/0 | 1826 | 2197 | 2700 | 0 | 0 | −9 | 1 2   4 |
| 02 | 0.03 | M/56 | Stricture | 120/0 | 1348 | 2162 | 3500 | 712 | 74 | 72 | 1 2 |
| 03 | 0.03 | M/32 | CD | UNK/30 | 852 | 1597 | 1300 | 9440 | −10 | 73 | 1 |
| 04 | 0.10 | M/37 | CD | UNK/0 | 4636 | 6275 | 2000 | 14312 | −31 | 15 | 1 2 |
| 05 | 0.10 | F/58 | MI | 40/0 | 4787 | 5988 | 3167 | 8150 | 5 | −13 | 1 2 |
| 06 | 0.10 | F/58 | CD | 70/0 | 4580 | 5599 | 3500 | 6180 | 3 | 4 | 1 2   4 5 |
| 07 | 0.10 | F/74 | Volvulus | 70/0 | 2787 | 4451 | 2667 | 4500 | −1 | 3 | 1 2   4 5 |
| 08 | 0.10 | F/48 | CD | 150/0 | 1807 | 5972 | 333 | 0 | 5 | 9 | 1 2   4 5 |
| 10 | 0.15 | F/47 | CD | 150/0 | 3683 | 10874 | 1000 | 858 | −2 | −2 | 1 2   4 5 |
| 11 | 0.15 | M/65 | CD | 145/0 | 2237 | 4206 | 3000 | 6750 | −5 | −21 | 1 2 |
| 12 | 0.15 | M/51 | CD | 90/0 | 4887 | 10273 | 1500 | 5629 | −1 | −18 | 1 2     5 |
| 18C | 0.10 | F/63 | MI | 50/50 | 2843 | 8537 | 0 | 0 | −4 | −1 | 1  3 4 |
| 19C | 0.10 | M/27 | CD | 70/75 | 2290 | 6240 | 3167 | 6760 | 2 | −2 | 1  3 4 |
| 20C | 0.10 | F/39 | CD | 145/50 | 1893 | 5163 | 0 | 0 | −5 | −4 | 1  3 4 |
| 21C | 0.10 | F/45 | CD | 110/75 | 1807 | 2865 | 0 | 0 | −1 | 1 | 1  3 4 |
| 22C | 0.10 | M/36 | Injury | 25/50 | 2063 | 4880 | 2220 | 9540 | 4 | −7 | 1  3 4 |

C~Patients with Colon-in-Continuity (all other patients had jejunostomies)
CD~Crohn's disease.
MI~Mesenteric Infarction.
Rec.~Resection of ileum, i.e., >80 Rec.: More than 80 cm of small intestine has been resected.
Dietary Compliance: The Difference between Oral intake of Wet-Weight in percent of Baseline intake.
UNK: unknown

TABLE 2

Wet Weight: Fecal Excretion, Absolute and Relative Absorption

|  | Patient Groups | Total Patients (N) | Patients With Beneficial Effect | Baseline Day −3 to 0 Mean ± SD | Effect of Treatment (Treatment minus Baseline) mean ± SD | Effect at Follow up (Follow up minus Baseline) mean ± SD |
|---|---|---|---|---|---|---|
| Wet Weight | | | | | | |
| Fecal (g/day) | 2. SBS Patients with End-Jejunostomy | 10 | 8 | 3258 ± 1410 | −682 ± 911* | 278 ± 496 |
|  | 3. SBS Patients with ≥50% Colon | 5 | 5 | 2179 ± 415 | −822 ± 341** | −240 ± 426 |
|  | 4. SBS Patients, High Dietary Compliance | 10 | 9 | 2558 ± 938 | −769 ± 447*** | 93 ± 500 |
| Absorption (g/day) | 2. SBS Patients with End-Jejunostomy | 10 | 9 | 18 ± 1427 | 788 ± 551** | −218 ± 577 |
|  | 3. SBS Patients with ≥50% Colon | 5 | 5 | 1613 ± 1503 | 751 ± 328** | 352 ± 525 |
|  | 4. SBS Patients, High Dietary Compliance | 10 | 9 | 1023 ± 1369 | 746 ± 436*** | 24 ± 576 |
| Absorption (% of intake) | 2. SBS Patients with End-Jejunostomy | 10 | 8 | −7 ± 64 | 20 ± 18** | −9 ± 16 |
|  | 3. SBS Patients with ≥50% Colon | 5 | 5 | 31 ± 39 | 26 ± 16* | 17 ± 30 |
|  | 4. SBS Patients, High Dietary Compliance | 10 | 9 | 22 ± 34 | 23 ± 16** | 0 ± 27 |

Patients: 16 SBS Patients (11 with jejunostomy and 5 with colon in continuity). Patient No. 03 was thought to have had a jejunostomy, but was determined to have 30% colon and was excluded from the analysis.
Effect of treatment: paired t-test; treatment versus baseline.
*$p < 0.05$, $p < 0.01$, *$p < 0.001$.
Effect at follow up: paired t-test; follow up versus baseline, all non-significant $p > 0.05$.

TABLE 3

Urine Wet Weight

| | Patient Groups | Total Patients (N) | Patients With Beneficial Effect | Baseline Day −3-0 Mean SD | Effect of Treatment (Treatment minus Baseline) mean ± SD | Effect at Follow up (Follow up minus Baseline) mean ± SD |
|---|---|---|---|---|---|---|
| Wet Weight (g/day) | 2. SBS Patients with End-Jejunostomy | 10 | 8 | 1257 ± 339 | 680 ± 535** | 11 ± 287 |
| | 3. SBS Patients with ≥50% Colon | 5 | 5 | 1834 ± 663 | 461 ± 200** | −90 ± 281 |
| | 4. SBS Patients, High Dietary Compliance | 10 | 10 | 1509 ± 595 | 725 ± 394*** | 30 ± 285 |

Patients: 16 SBS Patients (11 with jejunostomy and 5 with colon in continuity). Patient No. 03 was thought to have had a jejunostomy, but was determined to have 30% colon and was excluded from the analysis.
Effect of treatment: paired t-test; treatment versus baseline.
*p < 0.05, p < 0.01, *p < 0.001.
Effect at follow up: paired t-test; follow up versus baseline, all non-significant p > 0.05.

TABLE 4

Energy: Fecal Excretion, Absolute and Relative Absorption

| | Patient Groups | Total Patients (N) | Patients With Beneficial Effect | Baseline Day −3-0 Mean ± SD | Effect of Treatment (Treatment minus Baseline) mean ± SD | Effect at Follow up (Follow up minus Baseline) mean ± SD |
|---|---|---|---|---|---|---|
| Energy | | | | | | |
| Fecal (kJ/day) | 2. SBS Patients with End-Jejunostomy | 10 | 8 | 5800 ± 2919 | −532 ± 1703 | 320 ± 1200 |
| | 3. SBS Patients with ≥50% Colon | 5 | 4 | 5536 ± 2074 | −1343 ± 916* | −997 ± 1713 |
| | 4. SBS Patients, High Dietary Compliance | 10 | 8 | 5678 ± 2539 | −1060 ± 1083* | −98 ± 1674 |
| Absorption (kJ/day) | 2. SBS Patients with End-Jejunostomy | 10 | 6 | 5962 ± 3562 | 363 ± 2656 | −800 ± 2958 |
| | 3. SBS Patients with ≥50% Colon | 5 | 5 | 7346 ± 2483 | 1027 ± 798* | 907 ± 1146 |
| | 4. SBS Patients, High Dietary Compliance | 10 | 9 | 6449 ± 2099 | 963 ± 1290* | 452 ± 1211 |
| Absorption (% of intake) | 2. SBS Patients with End-Jejunostomy | 10 | 6 | 50 ± 17 | 5 ± 20 | −6 ± 12 |
| | 3. SBS Patients with ≥50% Colon | 5 | 5 | 57 ± 14 | 10 ± 7* | 10 ± 17 |
| | 4. SBS Patients, High Dietary Compliance | 10 | 9 | 54 ± 14 | 8 ± 11* | 3 ± 16 |

Patients: 16 SBS Patients (11 with jejunostomy and 5 with colon in continuity). Patient No. 03 was thought to have had a jejunostomy, but was determined to have 30% colon and was excluded from the analysis.
Effect of treatment: paired t-test; treatment versus baseline.
*p < 0.05, p < 0.01, *p < 0.001.
Effect at follow up: paired t-test; follow up versus baseline, all non-significant p > 0.05.

We Claim:

1. A method for enhancing intestinal absorption in a patient with short bowel syndrome with colon-in-continuity with remnant small intestine, wherein the patient retains colon sufficient to produce at least about 10% of endogenous GLP-2 levels produced by a healthy individual in a fed state, comprising the step of administering to said patient a GLP-2 receptor agonist using a dosing regimen effective to enhance intestinal absorption, wherein said GLP-2 receptor agonist is selected from the group consisting of a GLP-2 peptide, a GLP-2 analog, a derivatized GLP-2 peptide or a derivatized GLP-2 analog.

2. The method according to claim 1, wherein said enhancement of intestinal absorption is an increase in at least one of a wet weight absorption compared to a baseline wet weight absorption and/or an energy absorption compared to a baseline energy absorption.

3. The method according to claim 2, wherein said patient has at least 25% colon-in-continuity with remnant small intestine.

4. The method according to claim 3, wherein said patient has at least 50% colon-in-continuity with remnant small intestine.

5. The method according to claim 4, wherein said patient has at least 75% colon-in-continuity with remnant small intestine.

6. The method according to claim 2, wherein said patient has colon sufficient to produce endogenous GLP-2 plasma levels of at least 5pmol/L in the fed state.

7. The method according to claim 6, wherein said patient has colon sufficient to produce endogenous GLP-2 plasma levels of at least 10pmol/L in the fed state.

8. The method according to claim 2, wherein said remnant small intestine has a length of at least 25 cm.

9. The method according to claim 8, wherein said remnant small intestine has a length of at least 50 cm.

10. The method according to claim 2, wherein said dosing regimen comprises daily administration of said GLP-2 receptor agonist.

11. The method according to claim 2, wherein said dosing regimen comprises administration of said GLP-2 receptor agonist over a period of at least 21 days.

12. The method according to claim 2, wherein said GLP-2 receptor agonist is a mammalian GLP-2.

13. The method according to claim 12, wherein said GLP-2 receptor agonist is human GLP-2.

14. The method according to claim 2, wherein said GLP-2 receptor agonist is a GLP-2 analog.

15. The method according to claim 14, wherein said GLP-2 receptor agonist is a human GLP-2 analog.

16. The method according to claim 15, wherein said GLP-2 receptor agonist is [Gly2]hGLP-2.

17. The method according to claim 10, wherein said GLP-2 receptor agonist is administered at a daily dose of from 5 to 500 μg/kg/day.

18. The method according to claim 1, wherein the patient's short bowel syndrome is secondary to at least one of: Crohn's disease, vascular ischemic disease, mesenteric infarction, malrotation, volvulous, trauma, injury, a congenital anomaly, or a stricture.

19. The method according to claim 18, wherein the patient's short bowel syndrome is secondary to Crohn's disease.

20. The method according to claim 18, wherein the patient's short bowel syndrome is secondary to a stricture.

21. The method according to claim 18, wherein the patient's short bowel syndrome is secondary to mesenteric infarction.

22. The method according to claim 18, wherein the patient's short bowel syndrome is secondary to volvulous.

23. The method according to claim 20, wherein the patient's short bowel syndrome is secondary to injury.

24. The method according to claim 1, wherein the patient produces at least about 20%, 30%, 40%, or 50% of the endogenous GLP-2 plasma levels produced by a healthy individual in the fed state.

25. The method according to claim 1, wherein the patient produces about 100% of the endogenous GLP-2 plasma levels produced by a healthy individual in the fed state.

26. A method according to claim 1, wherein the patient produces at least about 5, 10, 15, 20, 25, 30, 35, 40, 45, 50, 55, 60, 65, or 70 pmol/L endogenous GLP-2 plasma levels in the fed state.

* * * * *